(12) United States Patent
Wells et al.

(10) Patent No.: US 12,268,535 B2
(45) Date of Patent: Apr. 8, 2025

(54) LIGHT ASSEMBLIES AND METHODS FOR MAMMOGRAPHY AND TOMOSYNTHESIS IMAGING SYSTEMS

(71) Applicant: HOLOGIC, INC., Marlborough, MA (US)

(72) Inventors: Timothy N. Wells, Marlborough, MA (US); Juliette Buccilli, Marlborough, MA (US); Alan Rego, Marlborough, MA (US); Joseph Vartolone, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 640 days.

(21) Appl. No.: 17/279,364

(22) PCT Filed: Sep. 25, 2019

(86) PCT No.: PCT/US2019/053020
§ 371 (c)(1),
(2) Date: Mar. 24, 2021

(87) PCT Pub. No.: WO2020/069031
PCT Pub. Date: Apr. 2, 2020

(65) Prior Publication Data
US 2021/0401381 A1    Dec. 30, 2021

Related U.S. Application Data

(60) Provisional application No. 62/736,089, filed on Sep. 25, 2018.

(51) Int. Cl.
*A61B 6/04*    (2006.01)
*A61B 6/02*    (2006.01)
(Continued)

(52) U.S. Cl.
CPC ............ *A61B 6/0492* (2013.01); *A61B 6/025* (2013.01); *A61B 6/0414* (2013.01); *A61B 6/107* (2013.01); *A61B 6/502* (2013.01)

(58) Field of Classification Search
None
See application file for complete search history.

(56) References Cited

U.S. PATENT DOCUMENTS 5,068,887 A  *  11/1991  Hughes ................ G03B 42/042
                                                        378/170
7,792,245 B2 *   9/2010  Hitzke ................... A61B 6/107
                                                         378/37
(Continued)

FOREIGN PATENT DOCUMENTS

CN    102196772 A    9/2011
CN    202665567 U    1/2013
(Continued)

OTHER PUBLICATIONS

International Search Report and Written Opinion of the International Searching Authority for International Patent Application No. PCT/US2019/053020 mailed Jan. 24, 2020, 18 pages.
(Continued)

*Primary Examiner* — Edwin C Gunberg
(74) *Attorney, Agent, or Firm* — Merchant & Gould P.C.

(57) ABSTRACT

An imaging system includes an x-ray tube head, a support arm, and a compression system coupled to the support arm. The compression system is independently rotatable relative to the x-ray tube head and includes a compression paddle, a support platform, and an x-ray receptor. The imaging system also includes a light assembly coupled to the support arm and disposed above the compression paddle. The light assembly is configured to direct one or more beams of light towards the support platform.

17 Claims, 10 Drawing Sheets

(51) Int. Cl.
*A61B 6/10* (2006.01)
*A61B 6/50* (2024.01)

(56) References Cited

U.S. PATENT DOCUMENTS

| | | |
|---|---|---|
| 8,611,491 B2 | 12/2013 | Holler et al. |
| 10,595,954 B2 | 3/2020 | DeFreitas et al. |
| 2005/0195587 A1 | 9/2005 | Moctezuma |
| 2007/0036265 A1* | 2/2007 | Jing ............... A61B 6/4429 378/37 |
| 2007/0139799 A1* | 6/2007 | Ramsauer ......... A61B 6/0414 359/837 |
| 2009/0323892 A1 | 12/2009 | Hitzke et al. |
| 2011/0087132 A1 | 4/2011 | DeFreitas |
| 2012/0253200 A1 | 10/2012 | Stolka et al. |
| 2014/0294142 A1 | 10/2014 | Choi |
| 2020/0315711 A1 | 10/2020 | Richter |
| 2022/0087626 A1 | 3/2022 | Hunsdon |

FOREIGN PATENT DOCUMENTS

| | | |
|---|---|---|
| CN | 103402431 A | 11/2013 |
| CN | 107106100 A | 8/2017 |
| EP | 3692921 | 8/2020 |
| JP | 2008-023015 A | 2/2008 |
| JP | 2012019842 A * | 2/2012 |
| JP | 2012-050519 | 3/2012 |
| JP | 2015-178010 | 10/2015 |
| JP | 2022-502138 | 1/2022 |
| KR | 20160059943 | 5/2016 |
| WO | 2006/061357 A1 | 6/2006 |
| WO | 2017/056533 | 4/2017 |
| WO | 2020/069031 | 4/2020 |

OTHER PUBLICATIONS

Zimmermann, B. et al., "A novel tomographic optical breast imaging system to simultaneously co-register x-ray tomosynthesis", Biomedical Optics, 1-3 (Jan. 2014).

PCT International Preliminary Report on Patentability in International Application PCT/US2019/053020, mailed Jan. 8, 2021, 9 pages.

* cited by examiner

LIGHT ASSEMBLIES AND METHODS FOR MAMMOGRAPHY AND TOMOSYNTHESIS IMAGING SYSTEMS

CROSS-REFERENCE TO RELATED APPLICATIONS

This application is a National Stage Application of PCT/US2019/053020, filed Sep. 25, 2019, which claims the benefit of an priority to U.S. Provisional Patent Application No. 62/736,089, filed Sep. 25, 2018, the disclosures of which are hereby incorporated by reference herein in their entireties. To the extent appropriate, a claim of priority is made to each of the above disclosed applications.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technologist manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed in an imaging area on a breast support platform that typically is flat, and the paddle then compresses the breast, usually while a technologist or other health professional is holding the breast in place. The technologist may also manipulate the breast to ensure proper tissue coverage in the image receptor's field of view.

One known challenge in mammography and breast tomosynthesis is the positioning of the patient's breast by the technologist in the image receptor's field of view before compressing the breast. For example, the imaging room typically has dim lighting to increase patient comfort and reduce patient anxiety. Low light, however, makes the technologist's work around the imaging system much more difficult and can increase the time required for imaging procedures. For example, identifying the active imaging area, which at times generally corresponds to the size, shape, and location of a compression paddle. Additionally, identifying the field of view of the image receptor is often difficult when the x-ray source is moved out of position so that the technologist has access to the patient's breast and the compression system.

SUMMARY

In one aspect, the technology relates to an imaging system including: an x-ray tube head; a support arm; a compression system coupled to the support arm and independently rotatable relative to the x-ray tube head, wherein the compression system includes a compression paddle, a support platform, and an x-ray receptor; and a light assembly coupled to the support arm and disposed above the compression paddle, wherein the light assembly is configured to direct one or more beams of light towards the support platform.

In an example, the light assembly includes a cantilever support coupled to the support arm and a light structure coupled to the cantilever support. In another example, the light structure includes a ring with an opening defined therein, and when an x-ray beam is emitted from the x-ray tube head, the x-ray beam travels through the opening such that the ring is not in a field of view of a resulting x-ray image. In yet another example, the light structure is fixed to the cantilever support. In still another example, the light structure includes one or more light sources. In an example, at least one of the one or more light sources is articulated. In another example, at least one of the one or more light sources is collimated. In yet another example, the light assembly includes a face shield. In still another example, the face shield is slidingly coupled to the cantilever support and configured to move along the cantilever support and with respect to the light structure.

In another aspect, the technology relates to an imaging system including: a gantry; a compression system rotatably supported on the gantry, wherein the compression system includes a compression paddle, a support platform, and an x-ray receptor disposed below the support platform; an x-ray tube head rotatably supported on the gantry and independently rotatable relative to the compression system; and an emitter configured to emit a visible position marker onto the support platform, wherein the emitter is disposed on the compression system.

In an example, the emitter includes a face shield. In another example, the emitter includes a ring extending from the compression system. In yet another example, the emitter includes at least one of an articulator and a collimator. In still another example, the emitter includes a laser light. In an example, the position marker includes a substantially linear line. In another example, the line corresponds to a front edge of the x-ray receptor.

In another aspect, the technology relates to a method of compressing a breast for an imaging procedure, the method including: illuminating a support platform of an imaging system by one or more light sources disposed on a light assembly, wherein the light assembly is coupled to a compression system; positioning the breast on the support platform; advancing a compression paddle towards the breast positioned on the support platform; and contacting at least a portion of the breast with the compression paddle.

In an example, the method further includes moving a face shield of the light assembly towards a retracted position, the face shield being moveable relative to the one or more light sources. In another example, illuminating the support platform includes emitting a position marker from the one or more light sources, the emitted position marker substantially visibly identifying a position of an imaging area on the support platform. In yet another example, the emitted position marker corresponds to a position of an x-ray receptor relative to the support platform during the imaging procedure. In still another example, the emitted positon marker includes a substantially linear line that corresponds to a front edge of an x-ray receptor. In an example, the emitted position marker includes at least one target marker identifying a target breast placement location on the support platform for positioning the breast. In another example, positioning the breast includes aligning at least a portion of the breast with the position marker.

In another aspect, the technology relates to a method of identifying an imaging area for an imaging system including: (a) a gantry, (b) a compression system including a compression paddle, a support platform, and an x-ray receptor disposed below the support platform, wherein the compression system is rotatable relative to the gantry, and (c) an x-ray tube head independently rotatable to the gantry and the compression system, the method including: rotating the compression system to a compression position; rotating the x-ray tube head to an access position, wherein when in the access position, the x-ray tube head is disposed at a non-orthogonal angle to the breast platform; emitting a position marker from an emitter disposed on the x-ray tube head towards the breast platform, wherein the emitted position marker substantially visibly delineates a position of the imaging area during an imaging procedure; rotating the x-ray source tube head to an imaging positon; and performing an imaging procedure.

In an example, the emitted position marker corresponds to a position of the x-ray receptor relative to the breast platform. In another example, the emitted position marker includes at least one target marker identifying a target breast placement location on the breast platform for a patient's breast. In yet another example, the at least one target marker corresponds to the target breast placement location for one or more of a nipple line, a skin line, and an axilla tissue line for the patent's breast. In still another example, the method further includes articulating the emitter relative to the x-ray tube head prior to emitting the position marker. In an example, the method further includes collimating the emitted position marker. In another example, rotating the x-ray tube head to the access position includes rotating the x-ray tube head relative to the compression paddle such that the compression paddle is not in a field of view of the emitter.

In another aspect, the technology relates to a method of illuminating an active imaging area for an imaging system including: (a) a gantry, (b) a compression system including a compression paddle, a support platform, and an x-ray receptor disposed below the support platform, wherein the compression system is rotatable relative to the gantry, and (c) an x-ray tube head independently rotatable to the gantry and the compression system, the method including: rotating the compression system to a first rotation position; rotating the x-ray tube head to a second rotation position, wherein when in the second rotation position, the x-ray tube head is disposed at a non-imaging position relative to the breast platform; emitting a position marker from a light source disposed on the compression system towards the breast platform, wherein the emitted position marker substantially visibly delineates a position of the active imaging area; rotating the x-ray source tube head to an imaging positon; and performing an imaging procedure.

In an example, the first rotation position is a MLO imaging position. In another example, the second rotation position is at a non-orthogonal angle to the breast platform. In yet another example, the active imaging area is based at least in part on a size, a shape, and/or a position of the compression paddle.

In another aspect, the technology relates to an imaging system including: an x-ray tube head; a support arm; a compression system coupled to the support arm and independently rotatably relative to the x-ray tube head, wherein the compression system includes a compression paddle, a support platform, and an x-ray receptor; and a projector coupled to the support arm and disposed above the compression paddle, wherein the projector is configured to project an image towards the support platform.

In an example, the imaging system further includes a face shield, and the projector is coupled to the face shield. In another example, the imaging system further includes a cantilever support, and the projector is coupled to the cantilever support. In yet another example, the projector is coupled in communication to a system control and work station unit of the imaging system. In still another example, the image projected by the projector at least partially aligns with an x-ray field of the x-ray tube head. In an example, the image projected by the projector includes one or more of a white box, a cross hair pattern, and one or more targets.

In another aspect, the technology relates to a method of compressing a breast for an imaging procedure, the method including: illuminating a support platform of an imaging system by a projector coupled to a compression system, wherein the illumination is provided by one or more images projected towards the support platform by the projector; positioning the breast on the support platform; advancing a compression paddle towards the breast positioned on the support platform; and contacting at least a portion of the breast with the compression paddle.

In an example, the one or more images projected towards the support platform by the projector substantially aligns with an x-ray field of an x-ray tube head, and the method further includes verifying that a patient is not within the x-ray field after the breast is positioned on the support platform. In another example, illuminating the support platform includes projecting one or more of a white box, a cross hair pattern, and one or more targets.

DETAILED DESCRIPTION

Figure 1A:
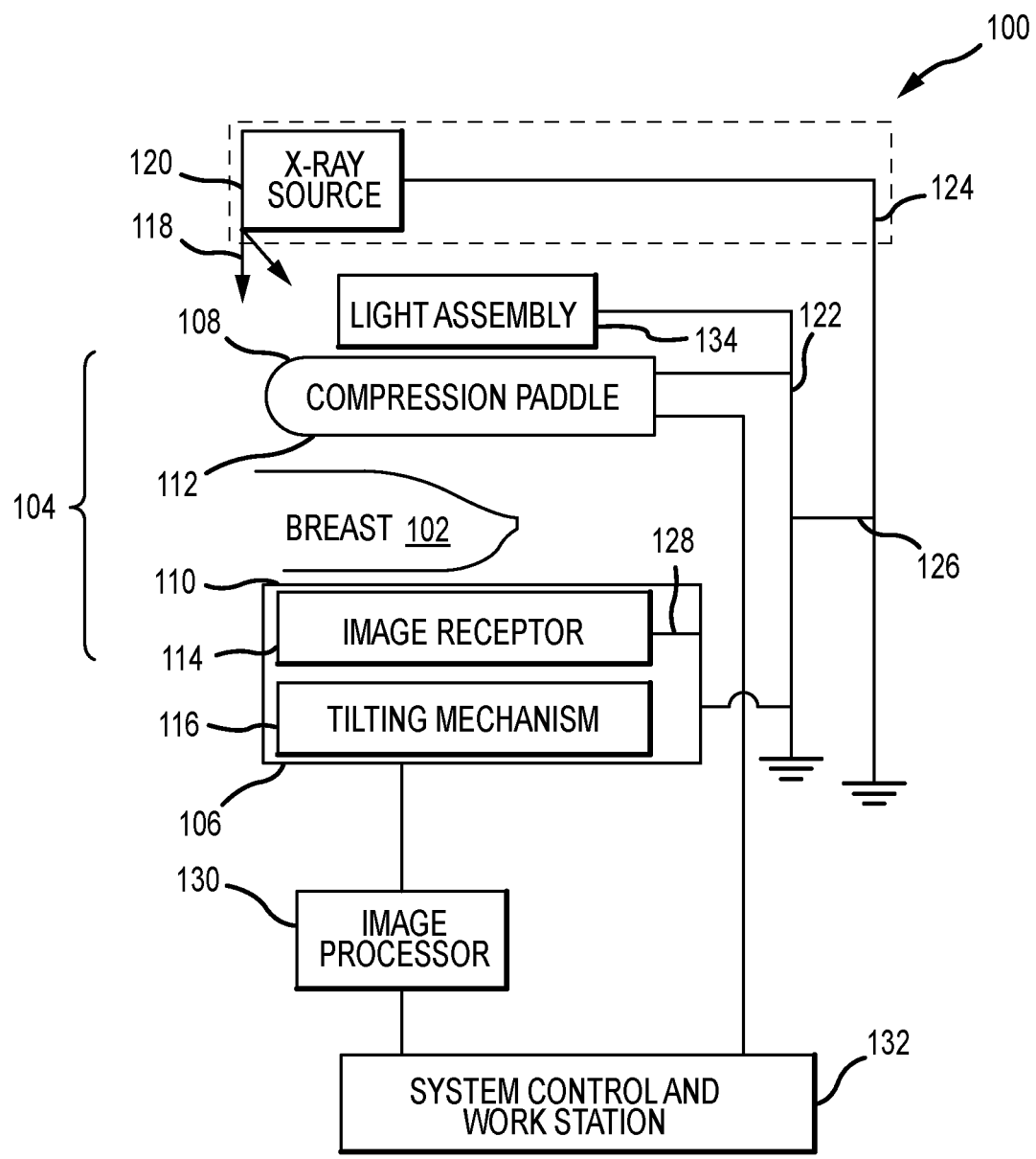
FIG. 1A is a schematic view of an exemplary imaging system.
Figure 1B:
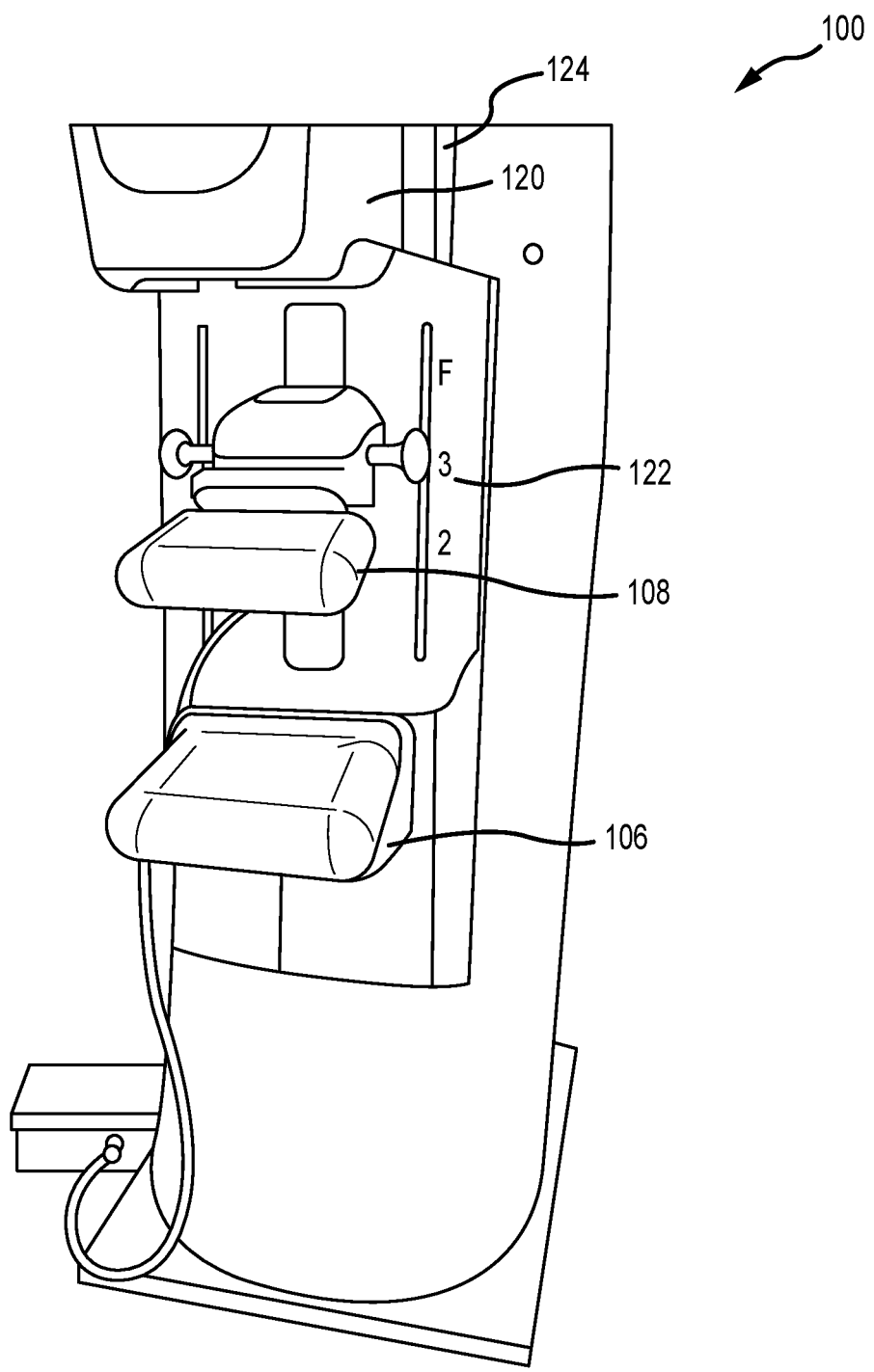
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 is configured to immobilize a patient's breast 102 for x-ray imaging (either or both of mammography and tomosynthesis) via a breast compression immobilizer unit or compression system 104. In the example, the compression system 104 includes a static breast support platform 106 and a moveable compression paddle 108. The breast support platform 106 and the compression paddle 108 each have a compression surface 110 and 112, respectively, with the compression surface 112 configured to move towards the support platform 106 to compress and immobilize the breast 102. In known systems, the compression surfaces 110, 112 are exposed so as to directly contact the breast 102. The support platform 106 also houses an image receptor 114 and, optionally, a tilting mechanism 116. The immobilizer unit 104 is in a path of an imaging x-ray beam 118 emanating from an x-ray source 120, such that the beam 118 impinges on the image receptor 114.

The compression system 104 is supported on a first support arm 122 and the x-ray source 120 is supported on a second support arm, also referred to as a tube arm 124. For mammography, support arms 122 and 124 can rotate as a unit about an axis 126 between different imaging orientations such as cranial-caudal (CC) and mediolateral oblique (MLO) views, so that the imaging system 100 can take a mammogram projection image at each orientation. In operation, the image receptor 114 remains in place relative to the support platform 106 while an image is taken. The immobilizer unit 104 releases the breast 102 for movement of support arms 122, 124 to a different imaging orientation. For tomosynthesis, the support arm 122 stays in place, with the breast 102 immobilized and remaining in place, while at least the tube arm 124 rotates the x-ray source 120 relative to the immobilizer unit 104 and the compressed breast 102 about the axis 126. The imaging system 100 takes plural tomosynthesis projection images of the breast 102 at respective angles of the x-ray beam 118 relative to the breast 102. As such, the compression system 104 and tube arm 124 may be rotated discrete from each other, unless matched rotation is required or desired for an imaging procedure.

Concurrently and optionally, the image receptor 114 may be tilted relative to the breast support platform 106 and coordinated with the rotation of the second support arm 124. The tilting can be through the same angle as the rotation of the x-ray source 120, but may also be through a different angle selected such that the x-ray beam 118 remains substantially in the same position on the image receptor 114 for each of the plural images. The tilting can be about an axis 128, which can but need not be in the image plane of the image receptor 114. The tilting mechanism 116 that is coupled to the image receptor 114 can drive the image receptor 114 in a tilting motion. For tomosynthesis imaging and/or CT imaging, the breast support platform 106 can be horizontal or can be at an angle to the horizontal, e.g., at an orientation similar to that for conventional MLO imaging in mammography. The imaging system 100 can be solely a mammography system, a CT system, or solely a tomosynthesis system, or a "combo" system that can perform multiple forms of imaging. One example of such a combo system has been offered by the assignee hereof under the trade name Selenia Dimensions.

When the system is operated, the image receptor 114 produces imaging information in response to illumination by the imaging x-ray beam 118, and supplies it to an image processor 130 for processing and generating breast x-ray images. A system control and work station unit 132 including software controls the operation of the system and interacts with the operator to receive commands and deliver information including processed-ray images.

One challenge with the imaging system 100 is how to efficiently position the breast 102 on the support platform 106 such that the patient's breast 102 can be compressed and immobilized for the desired or required imaging. For example, a health professional, typically an x-ray technologist, generally places the breast 102 on the support platform 106. The technologist will adjust the position of the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112. However, if the patient's breast is not properly positioned within the imaging area of the imaging system 100, then the breast compression procedures may be required to be redone, thus increasing patient discomfort and anxiety. Additionally, an improperly positioned breast may require an x-ray image to be retaken, which then may deliver an unnecessary x-ray dose. Furthermore, once the patient's breast is immobilized on the imaging system 100, the patient (e.g., hair, arms, etc.) also needs to positioned by the technologist out of the path (e.g., the x-ray field) of the x-ray source 120.

The technologies described herein relate to a breast compression and imaging system that utilizes a light assembly to aid the technologist in positioning the patient's breast for compression and imaging. Some of these technologies provide general illumination to the compression system, which aids the technologist when working with the patient and the imaging system. By illuminating the working area, the technologist can more efficiently position the patient. This can increase the overall efficiency of the imaging procedure, which also increases overall patient comfort. Other light assembly technologies described herein provide visible position markers that enable proper placement and/or compression of the breast such that the immobilization and imaging procedures are more efficient to perform. This can also help reduce patient discomfort associated with compression and the imaging process. These technologies generally improve the accuracy of breast placement and/or compression, enabling the technologist to more efficiently ensure proper immobilization and subsequent imaging.

As described herein, the technologies mainly utilize one or more light sources, preferably, visible light sources, coupled to the compression system 104. These light sources are configured to illuminate the breast support platform 106 to aid the technologist when working around the compression system 104. Additionally or alternatively, the light source can provide one or more position markers on the breast support platform 106 to more specifically aid the technologist in positioning and/or compressing the patient's breast in a proper position for the imaging process. For example, the position markers may correspond to a position of the image receptor 114, which is not visible to the technologist as it is below the support platform 106. In other examples, the position markers may correspond to an active imaging area that is a subset of the image receptor 114 to provide a more focused position aid for the technologist. Examples of the light sources can include, but are not limited to, light emitting diodes, laser lights, incandescent lamps, and even optical devices such as image projector systems.

Imaging systems 100 including any one of the light sources that perform the functions described herein are contemplated, although certain systems may include all of the described light sources, or additional light sources that are positioned differently but that perform the various functions described herein. In certain examples, the light sources described herein may perform a single described function or a plurality of functions.

Returning to FIG. 1A, the imaging system 100 is typically disposed within a patient room that is dimly lit to increase patient comfort and reduce patient apprehension. As such, a light assembly 134 may be coupled to the support arm 122 so that a light source can be provided in the system 100 and aid the technologist with positioning the patent within the compression system 104. The light assembly 134 generally points in a downward direction towards the compression paddle 108, breast 102, and the support platform 106. Functions performed in conjunction with the light assembly 134 are described herein and may include providing a light source on the compression system 104 for assisting the technologist with breast 102 positioning and compression. In some examples, the light assembly 134 is configured to not interfere with the x-ray beams 118 during the imaging procedures. In other examples, at least a portion of the light assembly 134 may be extended and/or retracted relative to the support arm 122, such that full access to the compression system 104 is provided to the technologist, and/or interference with the x-ray beam 118 during imaging procedures is reduced. In another example, the light assembly 134 may be storable at least partially within the support arm 122. Additionally or alternatively, the light assembly 134 may be configured to emit one or more position markers on the support platform 106 so as to identify an image area, an active image area, and/or specific breast placement location and further aid the technologist with positioning and compression of the breast. By increasing proper breast position and compression, patient comfort during the imaging procedure is increased and anxiety is reduced. Additional illumination systems are also depicted and described herein.

Figure 2A:
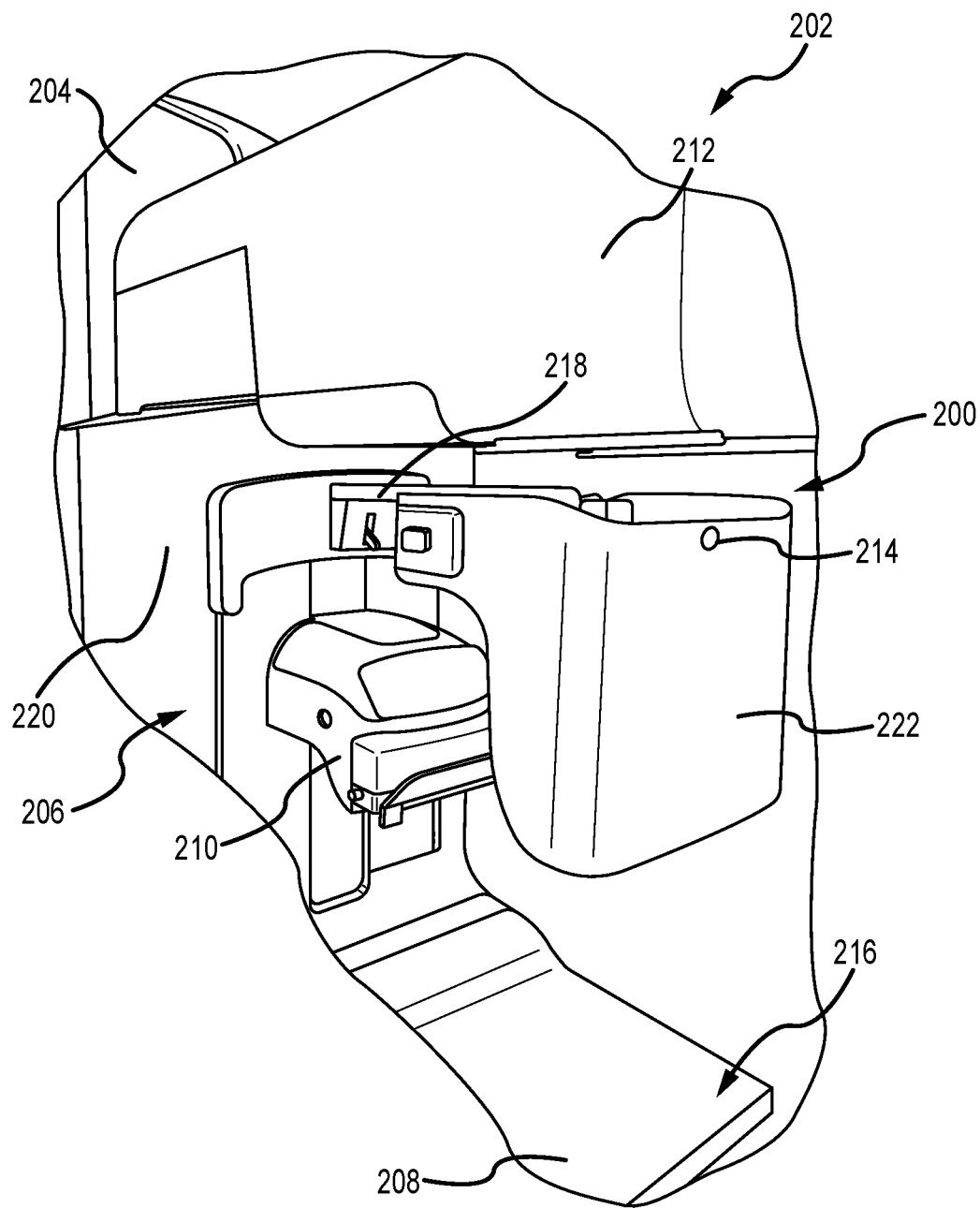
FIGS. 2A and 2B are perspective views of an exemplary light assembly in an extended and a retracted position, respectively.
Figure 2B:
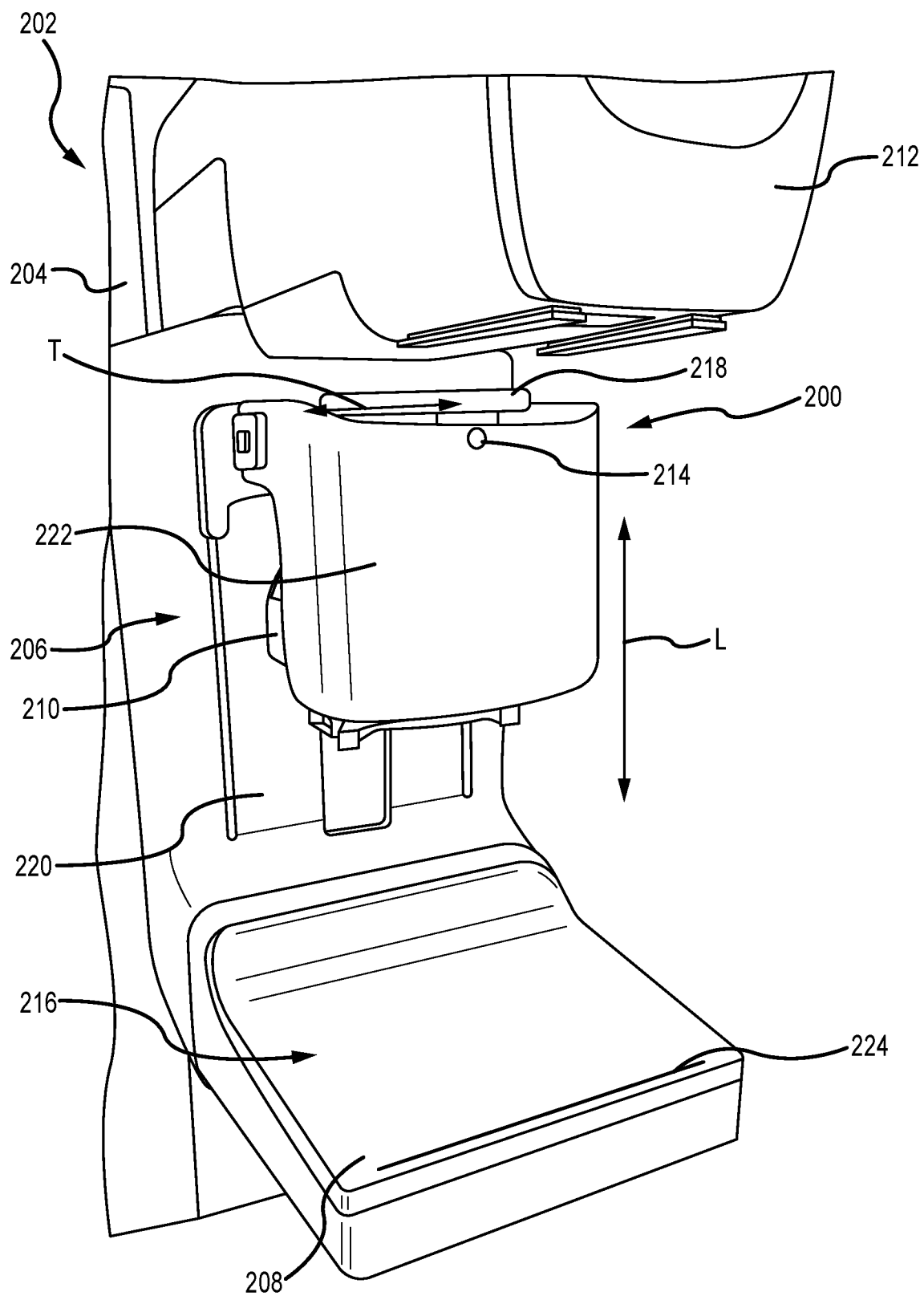

FIGS. 2A and 2B are perspective views of an imaging system 202 incorporating an exemplary light assembly 200 in an extended and a retracted position, respectively. Referring concurrently to FIGS. 2A and 2B and as described above, the imaging system 202 includes a gantry 204 that rotatably supports a compression system 206 having a support platform 208 and a compression paddle support 210 (a compression paddle is not shown for clarity). Additionally, the gantry 204 rotatably supports an x-ray tube head 212. In this example, the light assembly 200 is coupled to the compression system 206 such that the light assembly 200 can rotate therewith, relative to the gantry 204 and/or the x-ray tube head 212, and is positioned above the compression paddle support 210. The light assembly 200 includes one or more light sources 214 that are oriented so as to direct light beams towards an upper surface 216 of the support platform 208. By illuminating the upper surface 216, the technologist may more easily position the patient's breast within the compression system 206, even when the components of the imaging system 202 generate shadows over the support platform 208 and/or the compression paddle support 210.

In the example, the light source 214 may emit a general white light for illumination of area surrounding the support platform 208. For example, the light source 214 can be a light emitting diode (LED) lamp, an incandescent lamp, or the like. In other examples, the light source 214 may emit a colored light (e.g., red or blue) as required or desired. In another example, the light source 214 may be a laser that can provide a visible light. In some examples, the light source 214 may emit ultraviolet light and/or infrared light that can be used with additional imaging devices that are configured to make these light forms visible to the technologist. In yet further examples, the light source 214 may emit light that changes colors. For example, the light source 214 may change light colors based at least partially on the position of the patient's beast so as to indicate to the technologist that the breast is properly positioned on the support platform 208. Additionally or alternatively, the light source 214 may emit different light colors based on the area of the support platform 208 being illuminated.

In still further examples, the light source 214 may include an image projector configured to project an image towards the support platform 208. The image projector can include one or more of the following components: a light (e.g., LED, laser, etc.), an optical engine (e.g., Liquid Crystal Display (LCD), Digital Light Processing (DLP), etc.), an image input, a power input, a cooling system, a processor, and a focusing optic. The image projector can project still or video images as required or desired.

The light assembly 200 includes a cantilever support 218 that is coupled to a support arm 220 of the compression system 206. The cantilever support 218 can be removably coupled to the support arm 220 so that the light assembly 200 can be removed as required or desired. Additionally or alternatively, the cantilever support 218 can be slidingly coupled to the support arm 220 so that the light assembly 200 can move linearly L along the support arm 220 and be adjustable in height relative to the support platform 208 as required or desired. The cantilever support 218 extends from the patient facing end of the support arm 220 such that operation of the compression paddle support 210 is uninhibited. Furthermore, access is maintained to the compression system 206 from either the left or right side of the imaging system 202 for the patient and/or the technologist. The cantilever support 218 can be coupled in communication (e.g., power and/or data) to the imaging system 202 so that the system control and work station unit 132 (shown in FIG. 1A) can control the light source 214 as required or desired. The light assembly 200 can be a wired or wireless communication.

Attached to the free end of the cantilever support 218, the light assembly 200 may include a face shield 222. The face shield 222 is slidingly coupled to the cantilever support 218 so that it can move transversely T between an extended position (shown in FIG. 2A) and a retracted position (shown in FIG. 2B). In the extended position, the face shield 222 can be used to prevent the patient from moving into the x-ray beam emitted from the x-ray tube head 212 during imaging. The face shield 222 is substantially U-shaped such that the face shield 222 is not within a field of view of the x-ray image when it is in the extended position. In other examples, the face shield 222 may be lined with lead so as to provide radiation protection for the patient during the imaging procedures. Additionally, the face shield 222 remains stationary during tomosynthesis imaging since it is coupled to the support arm 220. The face shield 222 can also be retractable toward the retracted position so as to move the face shield 222 away from being positioned over the support platform 208 so that the technologist can more easily work while positioning and compressing the patient's breast.

In the example, the light source 214 is coupled to an inside surface of the face shield 222 so that patient contact with the light source 214 during use of the face shield 222 is prevented. Additionally, the light source 214 is substantially centered on the face shield 222 and aligned with the cantilever support 218. This position enables for a substantially uniform light distribution to be provided on the support platform 208 by the light assembly 200. In another example, the light source 214 may be disposed on the free end of the cantilever support 218. In some examples, more than one light source 214 may be spaced along the inside perimeter of the face shield 222. By using more than one light source 214, the light assembly 200 can independently operate each light source 214 such that the light distribution on the support platform 208 can be adjustable as required or desired. For example, light from each light source 214 may be directed towards one or more of the left side portion, the right side portion, the front portion, the back portion, and the center portion of the support platform 208.

Since the face shield 222 is moveable between two positions (e.g., extended and retracted), the light source 214 also moves between two positions. As such, one or more of the light sources 214 may be mounted on an articulator so that the light source 214 can be articulated. For example, articulating the light source 214 may include pivoting the light source 214 about one or more axes. In another example, articulating the light source 214 may include moving the light source 214 (e.g., in a linear and/or curvilinear range of motion) between two or more positions. This enables the light source 214 to be directed to the same location on the support platform 208 in both the extended and retracted positions, as well as at any positions between these extremes. Additionally or alternatively, one or more of the light sources 214 may be collimated so as to be directed to a specific location on the support platform 208. This enables undesirable light distribution away from the support platform 208 to be reduced and/or eliminated. For example, collimation of the light source 214 may include one or more optical lens that reflect and/or refract the light beam in a required or desired distribution pattern. Collimation of the light source 214 may also be induced by one or more angled mirrors in the light assembly 200. In another example, the collimated light may include a grid pattern illuminated over the upper surface 216 of the support surface 208 so as to aid the technologist in patient breast placement.

Furthermore, by collimating the light source 214 one or more position markers can be formed and directed on the support platform 208. The position marker is configured to aid the technologist in more specifically positioning the patient's breast on the support platform 208 for compression. In one example, the light source 214 can emit a position marker that corresponds to a position of the x-ray receptor relative to the support platform 208. This enables the technologist to have a visual aid to ensure that the patient's breast is positioned over the x-ray receptor. In another example, the emitted position marker can include a target marker that corresponds to a target breast placement location for one or more of a nipple line, a skin line, and an axilla tissue line. For example, the target marker may be a linear nipple line that the technologist can use to align the patient's nipple along on the support platform 208. The target marker can also be one or more lines, crosshatches, and/or shapes (e.g., square, circle, triangle, etc.) that define a general breast placement area on the support platform 208. The target marker may be a perimeter, or a partial perimeter, outline of a breast shape to define a breast placement area on the support platform 208. In still another example, the emitted position marker may correspond to an active imaging area, which can be based at least partially on the size, shape, and/or position of the compression paddle of the compression system 206. Regardless, any light source 214 may be used in the light assembly 200 that provides aid to the technologist and enables the patient's breast to be positioned more accurately and quickly while reducing the need for re-compression of the patient's breast.

In an aspect, the light source 214 can include a laser light that emits a light beam towards the support platform 208 and that forms a substantially linear line 224 (shown in FIG. 2B). In one example, the line 224 corresponds to a front edge of the x-ray receptor disposed within the platform 208, and thus, is positioned towards the front of the upper surface 216 of the support platform 208. By identifying the front edge of the receptor, the technologist can more easily position the patient's breast on the support platform 208 for compression. Additionally, the line 224 can project on the chest wall of the patient when the patient is positioned on the platform 208 so that the technologist can visualize the portion of the breast that is within the x-ray image area. In this example, the light source 214 emits a position marker, the line 224, and the position marker can also provide general illumination of the support platform 208 to assist the technologist in low light areas. In some examples, the laser light can be colored (e.g., red, green, etc.). In other examples, the laser light can be a white light as required or desired.

In the example, the light source 214 is disposed above the compression paddle on the support arm 220 so that it illuminates the support platform 208 from an above position. In this position, the light source 214 enables light to be directed in an orientation that at least partially aligns with an x-ray field of the x-ray tube head 212. As such, patient placement within the x-ray field and between the tube head 212 and the support platform 208 can easily be determined even when the tube head 212 is rotated out of an imaging position. In examples were the light source 214 includes a projector, the projector can project any image (still or motion) that enables the light assembly 200 to function as described herein. For example, a projection image may be a white box on a black background that corresponds to the x-ray receptor location within the platform 208. The position and size of the box can be completely flexible within the image space and there is no need for a mechanical shutter or other moving parts. A projector can project any desired shape, any size shape, any color, and is easily positionable (e.g., left or right side of the imaging area). This allows the light source 214 to provide any type of visual aid for the technologist. Further, the projector can project different patterns (e.g., a cross hair pattern for needle locations) or targets (e.g., an arrow for biopsy procedures) as required or desired. Additionally or alternatively, the light source 214 can have its intensity (e.g., brightness) be adjustable.

Figure 3:
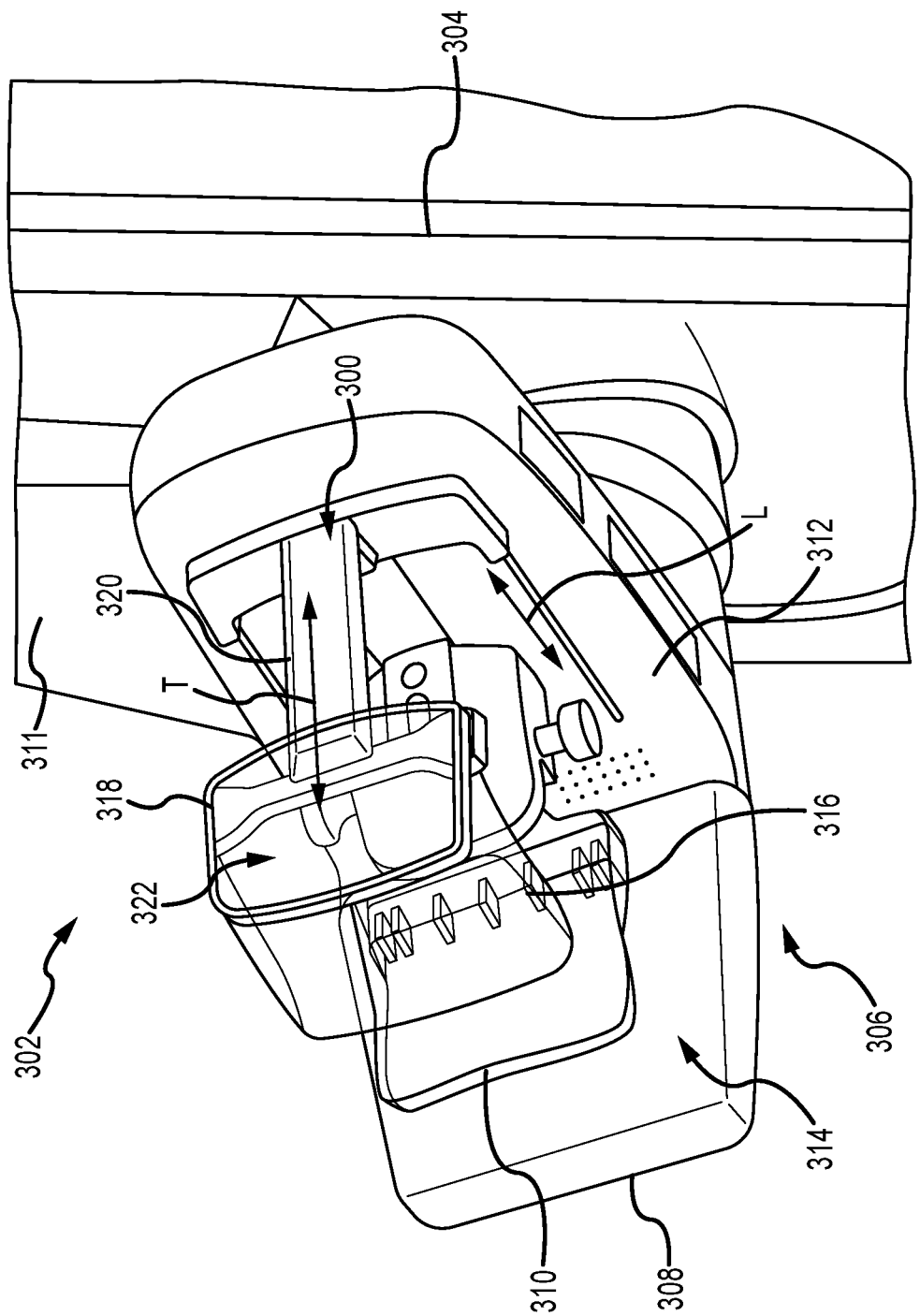
FIG. 3 is a perspective view of another light assembly.

FIG. 3 is a perspective view of an imaging system 302 including a different light assembly 300. As described above, the imaging system 302 includes a gantry 304 that rotatably supports a compression system 306 having a support platform 308 and a compression paddle 310. Additionally, the gantry 304 also rotatably supports an x-ray tube head (not shown for clarity but located at the top of a rotatable support arm 311). As illustrated in FIG. 3, the compression system 306 can be rotated to a MLO imaging procedure angle. The light assembly 300 is coupled to a support arm 312 of the compression system 306 such that the light assembly 300 can rotate therewith in relation to the gantry 304, and is positioned above the compression paddle 310. The light assembly 300 includes one or more light sources (not shown but disposed on a light structure 318) that are oriented so as to direct light beams towards an upper surface 314 of the support platform 308 as described above. The light sources can be LEDs, laser lights, a projector system, or any other light device as required or desired. In this example, however, the light assembly 300 includes a face shield 316 and the separate light structure 318, each independently coupled to the cantilever support 320.

The cantilever support 320 can linearly move L along the support arm 312 so that the light assembly 300 is adjustable in height as measured from the support platform 308. Additionally, the face shield 316 can transversely move T along the cantilever support 320 between an extended position and a retracted position as described above. The light structure 318 in this example, however, is disposed above the face shield 316 and fixed to the free end of the cantilever support 320 such that the light structure 318 remains fixed during movement of the face shield 316. This configuration of the light assembly 300 enables for one or more light sources disposed on the light structure 318 to maintain position above the support platform 308 regardless of the face shield 316 position. As such, the upper surface 314 of the support platform 308 is consistently illuminated so the technologist may more easily work around the compression system 306.

In the example, the light structure 318 may be substantially ring-shaped with an opening 322 defined therein. The ring may be substantially D-shaped (as shown in FIG. 3) with the long straight edge coupled to the cantilever support 320. In other examples, the ring may have any other shape as required or desired, for example, oval-shaped, circular-shaped, etc. The opening 322 is sized and shaped such that when the x-ray beam is emitted from the x-ray tube head, the x-ray beam travels through the opening 322 such that the light structure 318 is not in a field of view of the x-ray image that is formed. The ring is also large in size such that no matter its position L along the support arm 312, the light structure 318 is not in the field of view of the x-ray image. This enables for the light structure 318 to maintain is position above the support platform 308 during any imaging mode as required or desired, without forming undesirable artifacts in the x-ray image.

The light structure 318 may at least partially correspond to the perimeter shape of the top end of the face shield 316. That is, as shown in FIG. 3, when the face shield 316 is in its extended position, the light structure 318 aligns with the face shield 316 as if the light structure 318 is integral with the face shield 316. This enables for the ring and the opening 322 to be configured to not interfere with the x-ray beam during imaging procedures as is already for the face shield 316. Additionally, by aligning the light structure 318 and the face shield 316, patient contact with the light structure 318 is reduced or eliminated.

The one or more light sources on the light structure 318 may be disposed on the bottom surface of the ring such that they face the upper surface 314 of the support platform 308. In other examples, the one or more light sources may be disposed on the inside surface of the ring and angled towards the upper surface 314. As described above, the light sources can be LED lamps, incandescent lamps, lasers, projector, or the like, that emit white light, colored light, or any other light as required or desired. The light sources can also be articulated and/or collimated to direct the light to predetermined areas on the support platform 308. In the example, the upper surface of the ring may be configured as a heat sink so as to remove heat from the light sources. The light sources can provided a general working light for the technologist and aid in positioning and/or compressing the patient's breast. Additionally or alternatively, the light sources can provide a position marker (e.g., line(s), hash(s), point(s), outline(s), grid(s), etc.) for the technologist and aid in more specific alignment of the patient's breast for compression. This additional illumination generated by the light assembly 300 increases patient comfort during imagining procedures as the technologist is able to work more quickly and efficiently.

In some examples, the light structure may be configured to direct light towards the support platform 308 that corresponds to the image receptor area that corresponds to the imaging area. In other examples, the light structure 318 may be configured to direct light towards the support platform 308 that correspond to the active imaging area. For example, the active imaging area may be at least partially based on the size, shape, and/or position of the compression 310 on the compression system 306 and is generally a subset area of the larger imaging area. As such, the light sources may illuminate at least two portions, preferably two sides, of the active imaging area. The light structure 318 enables this illumination even when the x-ray tube head is moved to facilitate patient positioning, for example, during MLO positioning as described further below.

Figure 4A:
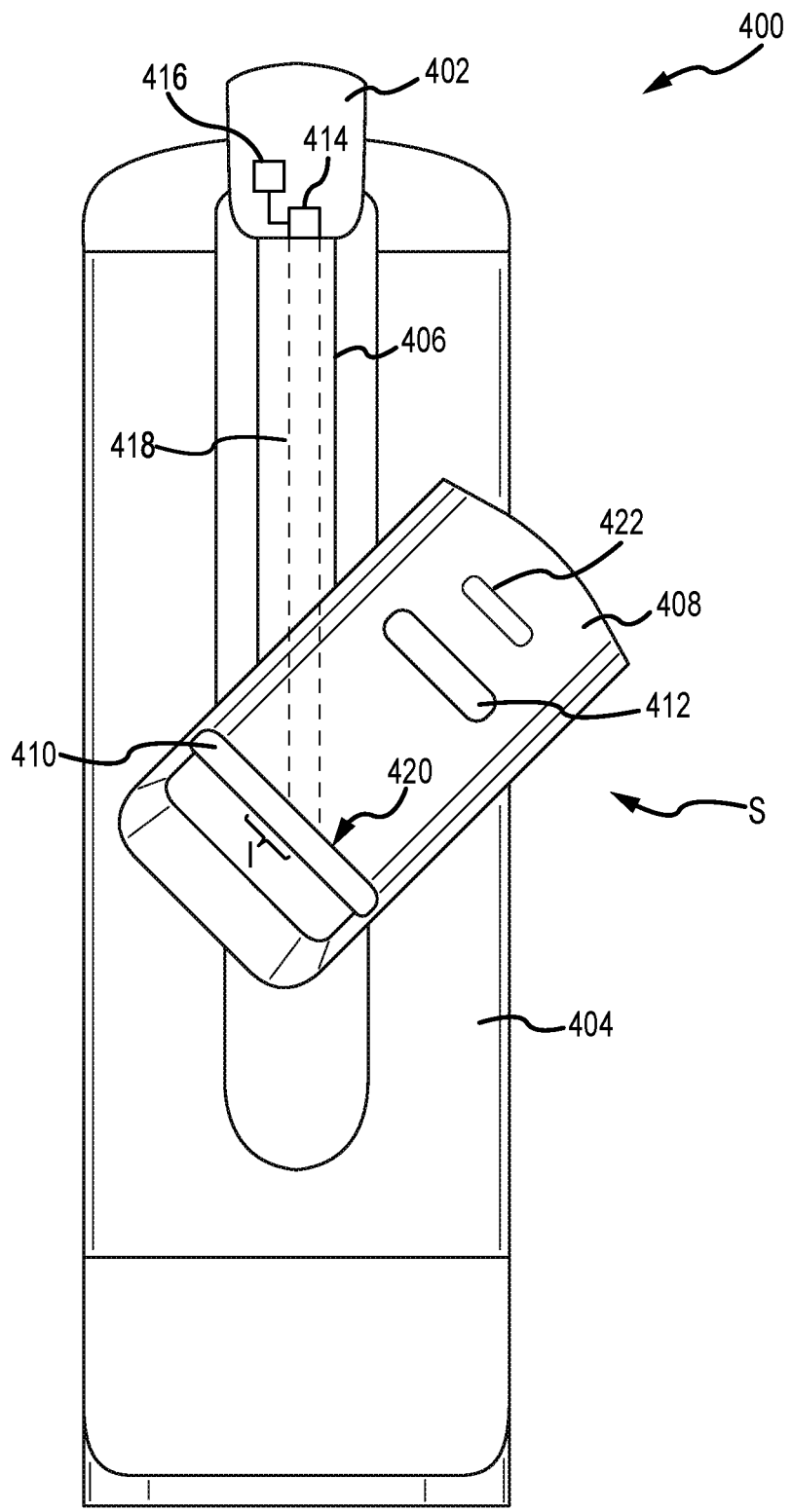
FIGS. 4A and 4B are front views of an imaging system having a tube head in a plurality of positions.
Figure 4B:
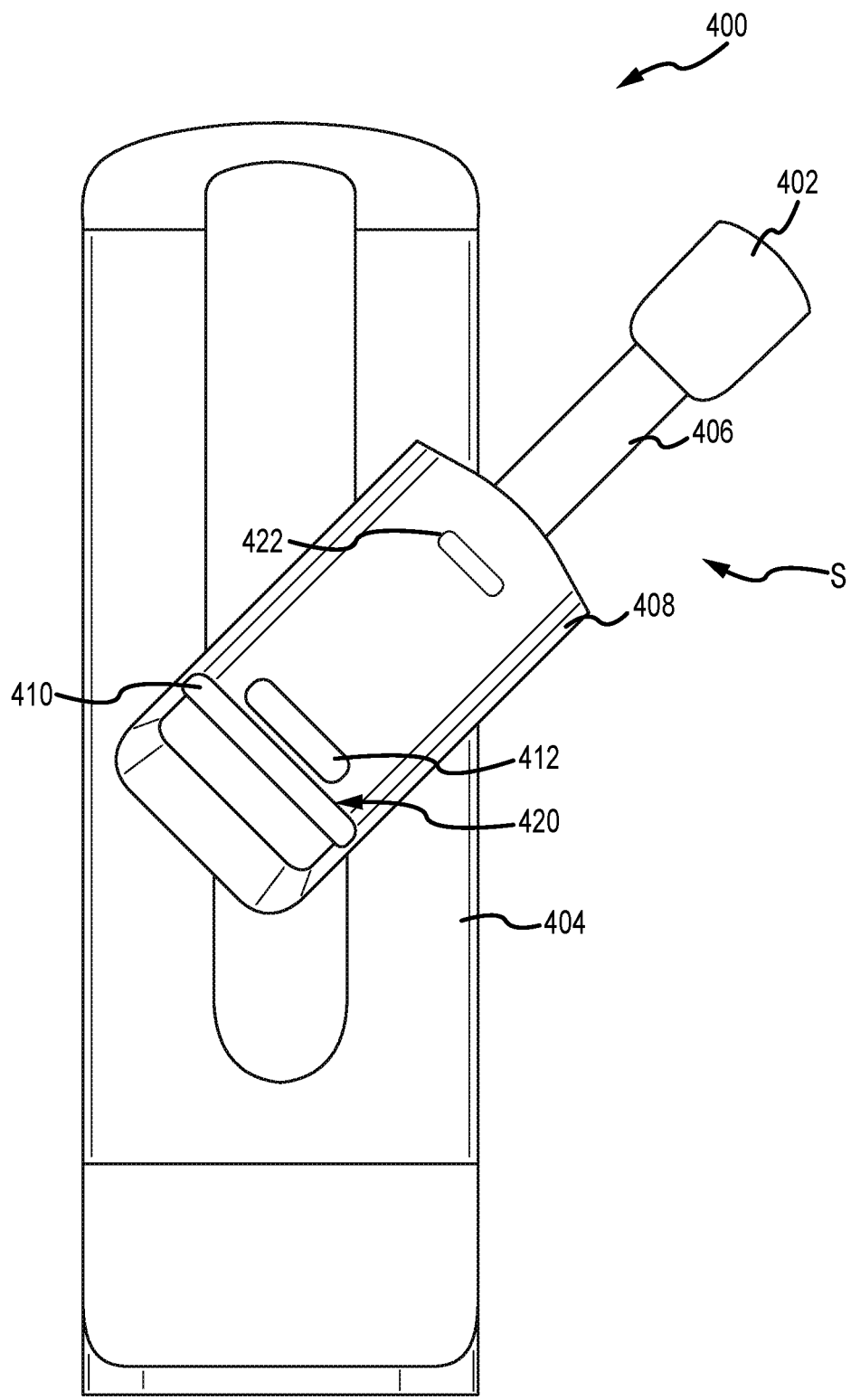

FIGS. 4A and 4B are front views of an imaging system 400 having a tube head 402 in a plurality of positions. FIGS. 4A-4B are generally described concurrently. The tube head 402 is rotatably coupled to a gantry 404 via a support arm 406. The imaging system 400 also includes a compression system 408 rotatably coupled to the gantry 404. The compression system 408 includes a breast support platform 410 and a compression paddle 412 that may be moved relative to (e.g., towards or away from) the support platform 410. Both the compression system 408 and tube head 402 are configured to rotate independently of each other. FIGS. 4A and 4B depict the compression system 408 in an angled position typically used for an MLO mammogram, but the imaging system 400 may also be used in conjunction with a tomosynthesis scan as required or desired.

One of the challenges associated with positioning the patient's breast, especially in advance of an MLO imaging procedure, is that the tube head 402 acts as an impediment to the technologist in positioning the breast. For example and referencing FIG. 4B, in some known prior art imaging systems, a positioning light can be emitted from the tube head 402 so as to mark an imaging area on the support platform 410. However, since the technologist generally stands to one side S of the gantry 404 to position the breast for compression, the position of the tube head 402 often requires the technologist to duck or crouch below the tube head 402 so as to position the breast between the support platform 410 and the compression paddle 412. This makes positioning of the breast in relation to the imaging area difficult because when the tube head 402 is rotated away from the compression system 408 the positioning light no longer aligns with the imaging area.

With reference now to FIG. 4A, the imaging system 400 includes a tube head emitter 414 disposed on or in the tube head 402. In some examples, the emitter 414 may be aligned with the x-ray beam source, while in other examples the emitter 414 may be offset from the x-ray beam source. The tube head emitter 414 is coupled to a mechanism 416 that is configured to articulate the direction of the tube head emitter 414. As such, the technologies described herein allow the imaging area (marked as I in FIG. 4A) to be properly marked, even when the tube head 402 is not directly aligned with the support platform 410. In order to determine the position of the imaging area I, a position encoder associated with the x-ray receptor disposed below the support platform 410 can communicate the location thereof to a remote or local controller of the tube head emitter 414.

In the example, the tube head emitter 414 emits visible or invisible light 418 that appears visible when impacting a support surface 420 of the support platform 410 for marking the image area I. Thus, the tube head emitter 414 more clearly visually identifies the imaging area I for the technologist to more efficiently position and compress the patient's breast, while still enabling access to the compression system 408 by the technologist. The light 418 may form a position marker upon the support platform 410 so as to delineate a position of the imaging area I during the imaging procedure. The position marker may correspond to a position of the x-ray receptor relative to the support platform 410. In another example, the position marker may include a target marker (e.g., a line(s), hash(s), point(s), outline(s), grid(s), etc.) used for aligning at least a portion of the patient's breast therewith. For example, the target marker may correspond to a nipple line, a skin line, or an axilla tissue line and aid in positioning the patient's breast. In some examples, the emitter 414 may emit a laser or a projection towards the support surface 420 to form the position marker. In other examples, collimated light may be emitted instead of a laser in order to form the position marker. In still another example, the emitted position marker may correspond to an active imaging area, which can be based at least partially on the size, shape, and/or position of the compression paddle 412.

In another example, an emitter 422 that is configured to emit a visual position marker as described above may be coupled to the compression system 408. This emitter 422 may include the light assemblies 200, 300 described above in reference to FIGS. 2A-3, or may be the emitter 414 just disposed at a different location on the imaging system 400. In either example, the emitter 422 may more clearly identify the imaging area I for the technologist to more efficiently position and compress the patient's breast. By locating the emitter 422 on the compression system 408, then the orientation of the position marker is more easily determined since the emitter 422 rotates with the compression system 408 and is aligned with the support platform 410. In another example, the emitter 422 may be coupled to the compression arm to which the compression paddle 412 is fixed. The emitter 422 may illuminate a general imaging area, such as an area defined by the x-ray receptor, illuminate a more specific active imaging area, such as an area defined by the compression paddle 412, or illuminate a target marker for more exact breast placement as required or desired.

Figure 5:
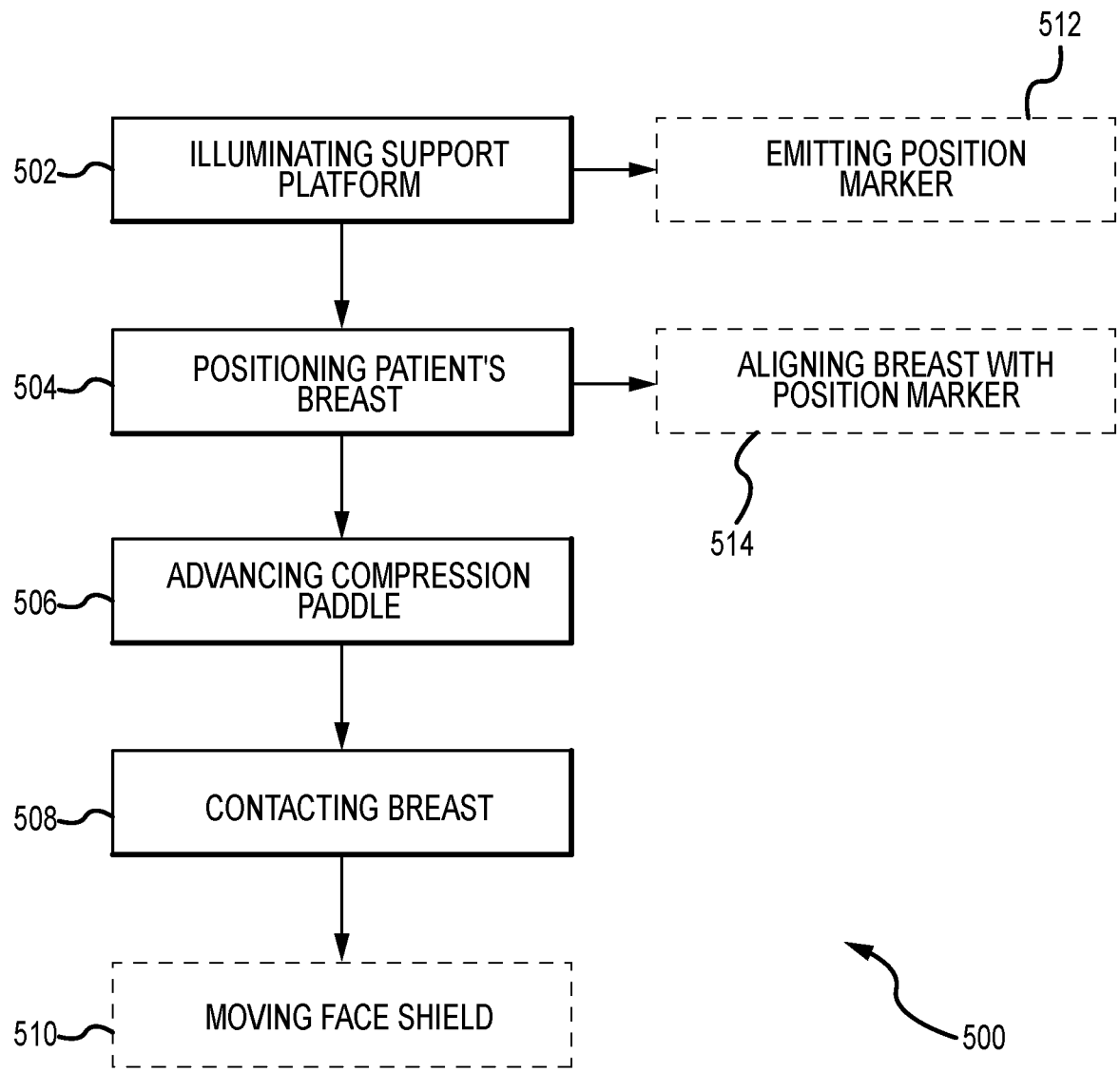
FIG. 5 depicts a flowchart illustrating a method of compressing a breast for an imaging procedure.

FIG. 5 depicts a flowchart illustrating a method 500 of compressing a breast for an imaging procedure. In the example, the method 500 begins with operation 502, illuminating a support platform of an imaging system by one or more light sources disposed on a light assembly. The light assembly may be coupled to a compression system of the imaging system. By illuminating the support platform, the technologist can be more efficient in working with the patient and manipulating the patient's breast. As described herein, the support platform can also be illuminated by a laser light or a projector that projects one or more images towards the support platform. In operation 502, the patient's breast is positioned on the support platform. Based on the position of the patient's breast, a compression paddle is advanced towards the support platform, operation 506. The patient's breast may then be contacted with the compression paddle, operation 508, so as to immobilize the breast for the imaging procedure. In some examples, the method 500 may further include moving a face shield of the light assembly towards a retracted position in operation 510. The face shield being moveable relative to the one or more light sources.

In general, the method 500 contemplates using a light source to illuminate the support platform to aid in the efficiency of the work of the technologist and improve patient experience. In some examples, the illumination may be a general working light that illuminates the working area (e.g., the support platform and compression paddle) of the technologist. In other examples, the illumination may be more targeted so that specific areas of the support platform are identified (e.g., an imaging area or active imaging area) to efficiently aid the technologist in positioning the patient's breast on the support platform and performing the compression of the breast for the subsequent imaging procedure. For example, in operation 512 illuminating the support platform (operation 502) may further include emitting a position marker from the one or more light sources such that the emitted position marker substantially visibly identifies a position of an imaging area on the support platform. In an aspect, the emitted positon marker can include a substantially linear line that corresponds to a front edge of an x-ray receptor. In another example, illuminating the support platform may include aligning the illumination with an x-ray field of an x-ray tube head so that the technologist can verifying that the patient is not within the x-ray field. For example, verify that the patient's hair is not within the x-ray field.

In order to determine the imaging area on the imaging system, data obtained from various sensors on the imaging system can be compared to known data from prior compressions, similar breasts, or similar procedures to identify an appropriate position marker. As such, the method 500 aids in increasing efficiencies for the technologist during the breast immobilization procedures so that patient comfort is increased. In one example, the emitted position marker may correspond to a position of an x-ray receptor relative to the support platform so that the patient's breast may be positioned appropriately over the x-ray receptor. In another example, the emitted position marker may include a target marker identifying a target breast placement location for the patient's breast. The target marker can be associated with a required or desired breast placement position on the support platform. This can include, for example, a nipple placement, a skin outline, an axilla tissue line, a scar placement, a mole placement, and the like. As such, positioning the patient's breast (operation 504) may include aligning at least a portion of the breast with the position marker, operation 514. In still another example, the emitted position marker may correspond to an active imaging area, which can be based at least partially on the size, shape, and/or position of the compression paddle of the compression system.

Additionally or alternatively, the position marker may indicate not only an initial breast position area to aid the technologist in breast placement on the support platform, but may also be used to indicate a required or desired compressed breast position. For example, the position marker may include a first marker indicating the position of the uncompressed patient's breast on the support platform and a corresponding second marker that indicates a position of the compressed patient's breast on the support platform. Once the second marker is reached (e.g., aligns) with at least a portion of the breast, this indicator may prompt the technologist to stop the breast compression. This will also increase patient comfort because it enhances the technologist's ability to not only position the breast, but to compress the breast to a comfortably, and clinically relevant, level of compression. The precise image area details provided by the light source generally allow for greater accuracy in both positioning and compression, enabling the technologist to provide reassurance and comfort to the patient during an often anxiety-inducing medical procedure. Thereafter, imaging may be performed of the compressed breast.

Figure 6:
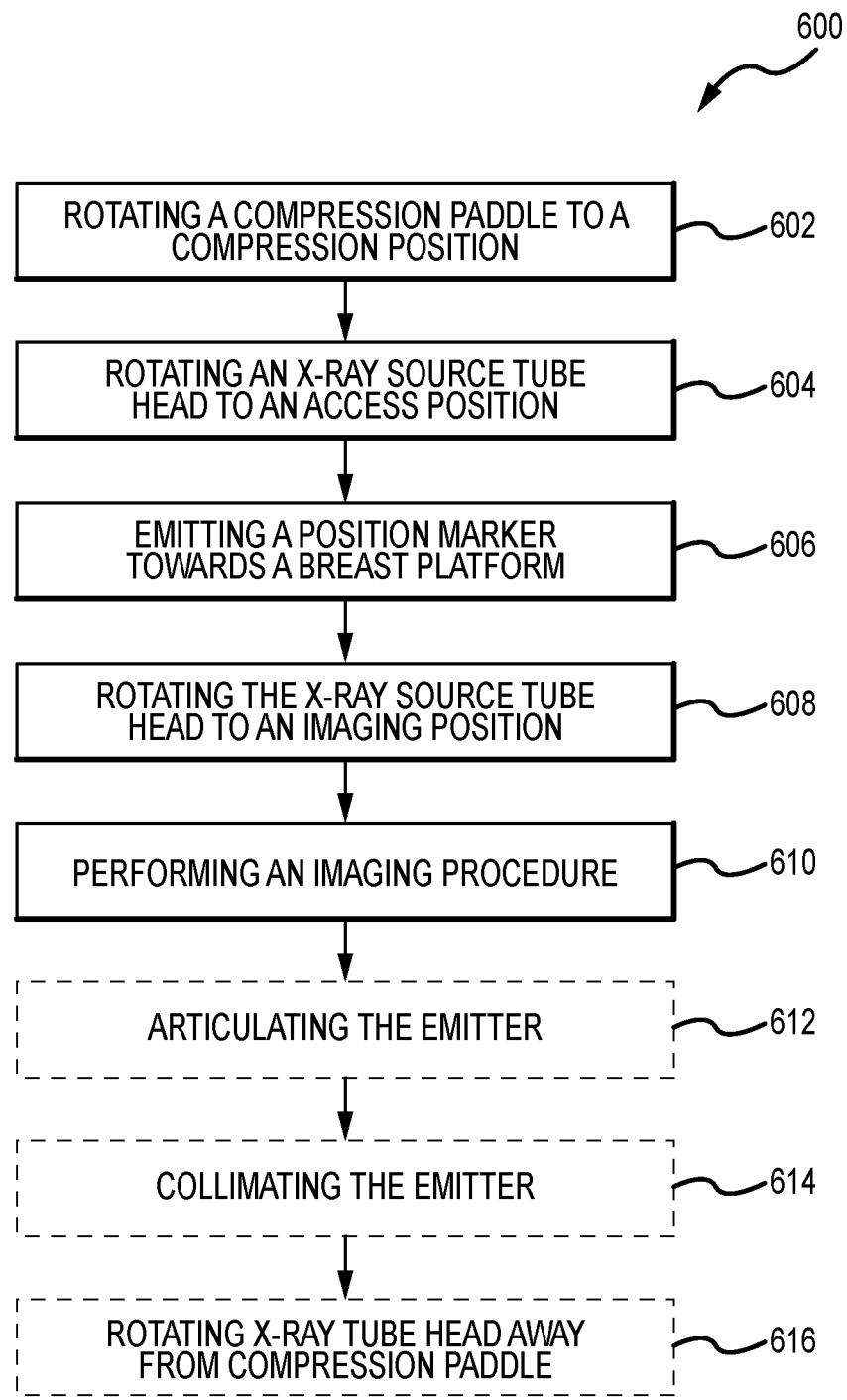
FIG. 6 depicts a flowchart illustrating a method of identifying an imaging area for an imaging system.

FIG. 6 depicts a flowchart illustrating a method 600 of identifying an imaging area for an imaging system. In general, the method 600 contemplates identifying an area for imaging on an imaging receptor, which may be useful for properly positioning a breast in an imaging system. This method 600 may be particularly useful when a tube head of an imaging system is disposed outside of a typical imaging position, such that proper positioning of the breast is more challenging for a technologist. The imaging system may be a breast imaging system such as those described herein that include a gantry and a compression system including a compression paddle, a support platform, and an x-ray receptor disposed below the support platform. The imaging system also includes an x-ray tube head independently rotatable to the gantry and the compression system, which is also rotatable relative to the gantry. The method 600 begins by rotating the compression system to a compression position, operation 602. This may be the position depicted, for example in FIG. 4A. In operation 604, the x-ray tube head is rotated to an access position, again as depicted in FIG. 4A. When in the access position, the x-ray tube head is disposed at a non-orthogonal angle to the breast platform. A position marker is emitted from an emitter disposed on the x-ray tube head towards the breast platform, operation 606. The emitted position marker substantially visibly delineates a position of the x-ray receptor during an imaging procedure. This allows for proper positioning of the breast by a technologist, without the need to duck or crouch under the x-ray tube head. Once the breast is properly positioned, the x-ray source tube head is rotated to an imaging positon, operation 608. The imaging position of the tube head is depicted in FIG. 4B. Thereafter, an imaging procedure may be performed, operation 610.

As described above, in one example, the emitted position marker may correspond to a position of an x-ray receptor relative to the support platform so that the patient's breast may be positioned appropriately over the x-ray receptor. In another example, the emitted position marker may include a target marker identifying a target breast placement location for the patient's breast. The target marker can be associated with a required or desired breast placement position on the support platform. This can include, for example, a nipple placement, a skin outline, an axilla tissue line, a scar placement, a mole placement, and the like. These markers allow for greater accuracy in positioning of the patient's breast, enabling the technologist to be more efficient during the compression procedure.

The method 600 may also further include articulating the emitter relative to the x-ray tube head prior to emitting the position marker, operation 612, such that the rotational offset between the compression system and the x-ray tube head is accounted for. In another example, the method 600 may include collimating the emitted position marker, operation 614, so as to reduce light dispersion away from the support platform. Furthermore, when rotating the x-ray tube head to the access position, the method 600 may include rotating the x-ray tube head relative to the compression paddle such that the compression paddle is not in a field of view of the emitter, operation 616. This ensures that the light emission is able to reach the support platform without being blocked by the compression paddle.

Figure 7:
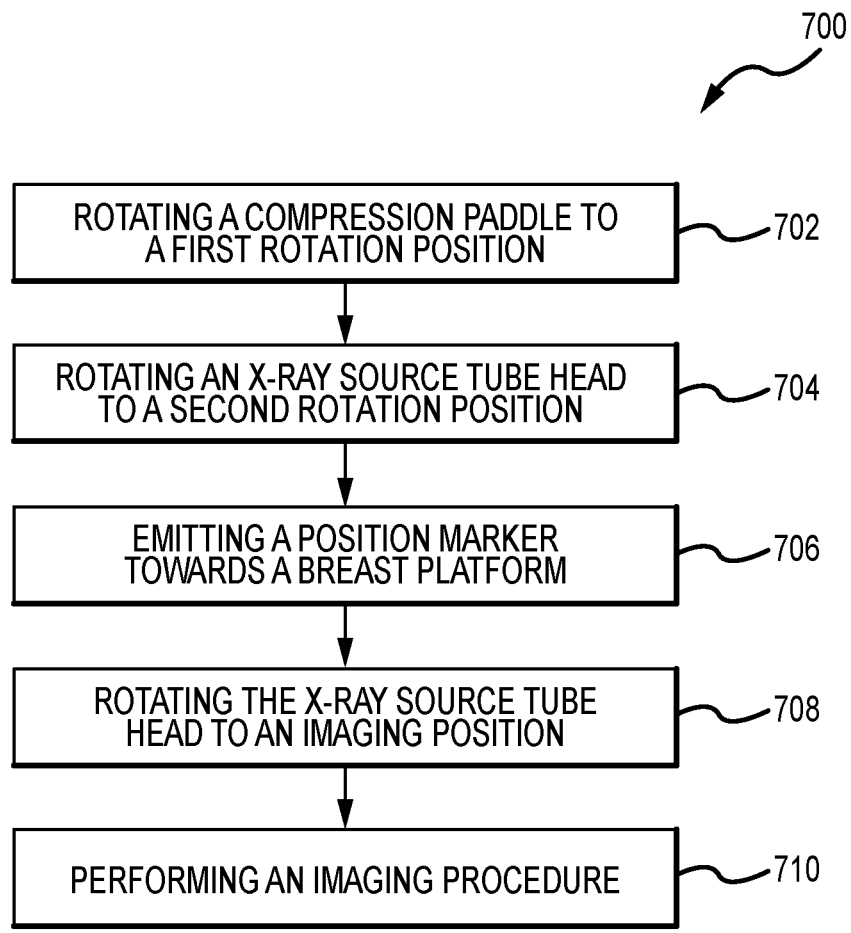
FIG. 7 depicts a flowchart illustrating a method of illuminating an active imaging area for an imaging system.

FIG. 7 depicts a flowchart illustrating a method 700 of illuminating an active imaging area for an imaging system. In general, the method 700 contemplates illuminating an active area, for example, based at least in part on a size, a shape, and/or a position of a compression paddle, which may be useful for properly positioning a breast in an imaging system. This method 700 may be particularly useful when a tube head of an imaging system is disposed outside of a typical imaging position, such that proper positioning of the breast is more challenging for a technologist. The imaging system may be a breast imaging system such as those described herein that include a gantry and a compression system including a compression paddle, a support platform, and an x-ray receptor disposed below the support platform. The imaging system also includes an x-ray tube head independently rotatable to the gantry and the compression system, which is also rotatable relative to the gantry. The method 700 begins by rotating the compression system to a first rotation position, operation 702. This may be the position depicted, for example, in FIG. 4A and corresponds to an MLO imaging procedure. In operation 704, the x-ray tube head is rotated to a second rotation position, again as depicted in FIG. 4A. When in the second rotation position, the x-ray tube head is disposed at a non-imaging position that is also at a non-orthogonal angle to the breast platform. A position marker is emitted from a light source disposed on the compression system towards the breast platform, operation 706. The emitted position marker substantially visibly delineates a position of the active image area. This allows for proper positioning of the breast by a technologist, without the need to duck or crouch under the x-ray tube head. Once the breast is properly positioned, the x-ray source tube head is rotated to an imaging positon, operation 708. The imaging position of the tube head is depicted in FIG. 4B. Thereafter, an imaging procedure may be performed, operation 710.

This disclosure describes some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art. Any number of the features of the different examples described herein may be combined into one single example and alternate examples having fewer than or more than all of the features herein described are possible. It is to be understood that terminology employed herein is used for the purpose of describing particular examples only and is not intended to be limiting. It must be noted that, as used in this specification, the singular forms "a," "an," and "the" include plural referents unless the context clearly dictates otherwise.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

The invention claimed is:

1. An imaging system comprising:
an x-ray tube head;
a support arm;
a compression system coupled to the support arm and independently rotatable relative to the x-ray tube head, wherein the compression system comprises a compression paddle, a support platform, and an x-ray receptor;
a cantilever support coupled to a patent facing surface of the support arm, the cantilever support having a length extending away from the support arm;
a face shield slidingly coupled to the cantilever support, wherein the face shield is configured to slide at least partially along the length of the cantilever support; and
a light assembly coupled to the face shield and disposed above the compression paddle, wherein the light assembly is configured to direct one or more beams of light towards the support platform, and wherein the light assembly is coupled to an inside surface of the face shield and aligned with the cantilever support.

2. The imaging system of claim 1, wherein the light assembly comprises a ring with an opening defined therein, and wherein when an x-ray beam is emitted from the x-ray tube head, the x-ray beam travels through the opening such that the ring is not in a field of view of a resulting x-ray image.

3. The imaging system of claim 1, wherein the light assembly comprises one or more light sources.

4. The imaging system of claim 3, wherein at least one of the one or more light sources is articulated.

5. The imaging system of claim 3, wherein at least one of the one or more light sources is collimated.

6. The imaging system of claim 1, wherein the light assembly moves with the face shield along the cantilever support.

7. An imaging system comprising:
a gantry;
a compression system rotatably supported on the gantry, wherein the compression system comprises a compression paddle, a support platform, and an x-ray receptor disposed below the support platform;
an x-ray tube head rotatably supported on the gantry and independently rotatable relative to the compression system;
a cantilever support coupled to the compression system, the cantilever support having a length extending away from the compression system;
a face shield slidingly coupled to the cantilever support, wherein the face shield is configured to slide at least partially along the length of the cantilever support; and
an emitter coupled to the face shield and configured to emit a visible position marker onto the support platform, and wherein the emitter is coupled to an inside surface of the face shield and aligned with the cantilever support.

8. The imaging system of claim 7, wherein the emitter moves with the face shield along the cantilever support.

9. The imaging system of claim 7, wherein the emitter comprises a ring extending from the compression system.

10. The imaging system of claim 7, wherein the emitter comprises at least one of an articulator and a collimator.

11. The imaging system of claim 7, wherein the emitter comprises a laser light.

12. The imaging system of claim 11, wherein the position marker comprises a substantially linear line.

13. The imaging system of claim 12, wherein the line corresponds to a front edge of the x-ray receptor.

14. A method of compressing a breast for an imaging procedure, the method comprising:
illuminating a support platform of an imaging system by one or more light sources disposed on a light assembly, wherein the light assembly is coupled to a face shield slidably supported on a cantilever support coupled to a compression system, the cantilever support having a length extending away from the compression system;
sliding the face shield at least partially along the length of the cantilever support based on patient position at the imaging system, wherein the light assembly is coupled to an inside surface of the face shield and aligned with the cantilever support;
positioning the breast on the support platform;
advancing a compression paddle towards the breast positioned on the support platform; and
contacting at least a portion of the breast with the compression paddle.

15. The method of claim 14, wherein illuminating the support platform comprises emitting a position marker from the one or more light sources, wherein the emitted position marker substantially visibly identifies a position of an imaging area on the support platform.

16. The method of claim 15, wherein the emitted position marker corresponds to a position of an x-ray receptor relative to the support platform during the imaging procedure.

17. The method of claim 15, wherein the emitted position marker comprises a substantially linear line that corresponds to a front edge of an x-ray receptor.

* * * * *